United States Patent
Sing et al.

(10) Patent No.: US 6,183,497 B1
(45) Date of Patent: Feb. 6, 2001

(54) ABSORBABLE SPONGE WITH CONTRASTING AGENT

(75) Inventors: Eduardo Chi Sing, Dana Point; Mark Ashby, Laguna Niguel, both of CA (US)

(73) Assignee: Sub-Q, Inc., San Clemente, CA (US)

( * ) Notice: Under 35 U.S.C. 154(b), the term of this patent shall be extended for 0 days.

(21) Appl. No.: 09/335,452

(22) Filed: Jun. 17, 1999

Related U.S. Application Data

(63) Continuation-in-part of application No. 09/071,670, filed on May 1, 1998, now Pat. No. 6,071,301, and a continuation-in-part of application No. 09/071,284, filed on May 1, 1998.

(51) Int. Cl.⁷ ..................................................... A61B 17/08

(52) U.S. Cl. ............................................................ 606/213

(58) Field of Search ..................................... 606/213, 215, 606/216; 604/51, 59–61, 48, 57, 38

(56) References Cited

U.S. PATENT DOCUMENTS

| | | |
|---|---|---|
| 581,235 | 4/1897 | Kenyon . |
| 1,578,517 | 5/1926 | Hein . |
| 2,086,580 | 7/1937 | Shirley . |
| 2,465,357 | 4/1949 | Correll . |
| 2,492,458 | 12/1949 | Bering, Jr. . |
| 2,507,244 | 5/1950 | Correll . |
| 2,558,395 | 6/1951 | Studer . |
| 2,597,011 | 5/1952 | MacMasters et al. . |
| 2,680,442 | 6/1954 | Linzmayer . |
| 2,761,446 | 9/1956 | Reed . |
| 2,814,294 | 11/1957 | Figge . |
| 2,824,092 | 2/1958 | Thompson . |
| 2,899,362 | 8/1959 | Sieger, Jr. et al. . |
| 3,157,524 | 11/1964 | Artandi . |
| 4,000,741 | 1/1977 | Binard et al. . |
| 4,323,072 | 4/1982 | Rosenbluth et al. . |
| 4,340,066 | 7/1982 | Shah . |
| 4,390,018 | 6/1983 | Zulowski . |
| 4,515,637 | 5/1985 | Cioca . |
| 4,587,969 | 5/1986 | Gillis . |
| 4,588,395 | 5/1986 | Lemelson . |
| 4,619,261 | 10/1986 | Guerriero . |
| 4,619,913 | 10/1986 | Luck et al. . |
| 4,645,488 | 2/1987 | Matukas . |
| 4,744,364 | 5/1988 | Kensey . |
| 4,790,819 | 12/1988 | Li et al. . |
| 4,829,994 | 5/1989 | Kurth . |

(List continued on next page.)

FOREIGN PATENT DOCUMENTS

| | | |
|---|---|---|
| 0 032 826 | 7/1981 | (EP) . |
| 0 476 178 | 3/1992 | (EP) . |
| 0 482 350 | 4/1992 | (EP) . |
| 2 641 692 | 7/1990 | (FR) . |
| 1 509 023 | 4/1978 | (GB) . |
| 1 569 660 | 6/1980 | (GB) . |
| 782 814 | 11/1980 | (SU) . |
| 1 088 709 | 4/1984 | (SU) . |
| 96/08208 | 3/1966 | (WO) . |
| 98/06346 | 2/1998 | (WO) . |

OTHER PUBLICATIONS

Product brochure for Gelfoam, Pharmacia & Upjohn, Sep. 1996

Product brochure for Gelfoam, Pharmacia & Upjohn, May 1997.

(List continued on next page.)

*Primary Examiner*—Michael Buiz
*Assistant Examiner*—(Vikki) Hoa B. Trinh
(74) *Attorney, Agent, or Firm*—Burns, Doane, Swecker & Mathis, L.L.P.

(57) ABSTRACT

An absorbable sponge containing a contrasting agent (e.g, radiopaque agent) that can be introduced to a biopsy tract or other puncture wound site is provided. The contrasting agent permits identification of the site by fluoroscopy or other imaging techniques.

30 Claims, 5 Drawing Sheets

U.S. PATENT DOCUMENTS

| | | |
|---|---|---|
| 4,850,960 | 7/1989 | Grayzel . |
| 4,852,568 | 8/1989 | Kensey . |
| 4,890,612 | 1/1990 | Kensey . |
| 4,900,303 | 2/1990 | Lemelson . |
| 4,929,246 | 5/1990 | Sinofsky . |
| 4,936,835 | 6/1990 | Haaga . |
| 4,950,234 | 8/1990 | Fujioka et al. . |
| 5,007,895 | 4/1991 | Burnett . |
| 5,021,059 | 6/1991 | Kensey et al. . |
| 5,053,046 | 10/1991 | Janese . |
| 5,061,274 | 10/1991 | Kensey . |
| 5,080,655 | 1/1992 | Haaga . |
| 5,108,421 | 4/1992 | Fowler . |
| 5,163,904 | 11/1992 | Lampropoulos et al. . |
| 5,167,624 | 12/1992 | Butler et al. . |
| 5,192,300 | 3/1993 | Fowler . |
| 5,192,301 | 3/1993 | Kamiya et al. . |
| 5,195,988 | 3/1993 | Haaga . |
| 5,220,926 | 6/1993 | Jones . |
| 5,221,259 | 6/1993 | Weldon et al. . |
| 5,275,616 | 1/1994 | Fowler . |
| 5,310,407 | 5/1994 | Casale . |
| 5,325,857 | 7/1994 | Nabai et al. . |
| 5,334,216 | 8/1994 | Vidal et al. . |
| 5,366,480 | 11/1994 | Corriveau et al. . |
| 5,383,896 | 1/1995 | Gershony et al. . |
| 5,383,899 | 1/1995 | Hammerslag . |
| 5,388,588 | 2/1995 | Nabai et al. . |
| 5,391,183 | 2/1995 | Janzen et al. . |
| 5,419,765 | 5/1995 | Weldon et al. . |
| 5,431,639 | 7/1995 | Shaw . |
| 5,437,631 | 8/1995 | Janzen . |
| 5,467,780 | 11/1995 | Nabai et al. . |
| 5,478,352 | 12/1995 | Fowler . |
| 5,479,936 | 1/1996 | Nabai et al. . |
| 5,486,195 | 1/1996 | Myers et al. . |
| 5,522,850 | 6/1996 | Yomtov et al. . |
| 5,526,822 | 6/1996 | Burbank et al. . |
| 5,529,577 | 6/1996 | Hammerslag . |
| 5,540,715 | 7/1996 | Katsaros et al. . |
| 5,545,178 | 8/1996 | Kensey et al. . |
| 5,558,853 | 9/1996 | Quay . |
| 5,591,204 | 1/1997 | Janzen et al. . |
| 5,591,205 | 1/1997 | Fowler . |
| 5,601,602 | 2/1997 | Fowler . |
| 5,645,566 | 7/1997 | Brennenman et al. . |
| 5,649,547 | 7/1997 | Ritchart et al. . |
| 5,653,730 | 8/1997 | Hammerslag . |
| 5,665,107 | 9/1997 | Hammerslag . |
| 5,681,279 | 10/1997 | Rober et al. . |
| 5,716,375 | 2/1998 | Fowler . |
| 5,725,498 | 3/1998 | Janzen et al. . |
| 5,741,223 | 4/1998 | Janzen et al. . |
| 5,769,086 | 6/1998 | Ritchert et al. . |
| 5,775,333 | 7/1998 | Burbank et al. . |
| 5,810,806 | 9/1998 | Ritchart et al. . |
| 5,830,130 | 11/1998 | Janzen et al. . |
| 5,902,310 | 5/1999 | Foerster et al. . |

OTHER PUBLICATIONS

David J. Allison, M.D., et al., "Percutaneous Liver Biopsy and Tract Embolization with Steel Coils," *Radiology*, vol. 169 (1988): 261–263.

Vincent Chuang, M.D., et al., "Sheath Needle for Liver Biopsy in High–risk Patients:Technical Developments and Instrumentation," *Radiology*, vol. 166 (1988) 261–262.

J.P.M. Foran, et al., "Early Mobilization After Percutaneous Cardiac Catheterisation Using Collagen Plug (VasoSeal) Hemostasis," *Br. Heart*, vol. 69 (1993): 424–429.

J.S.R. Gibbs, et al., "Femoral Arterial Hemostasis Using a Collagen Plug After Coronary Artery Stent Implantation," *Journal of Interventional Cardiology*, vol. 5, No. 2 (1992): 85–88.

Ferdinand Kiemeneij, M.D., et al., "Improved Anticoagulation Management After Palmaz Schatz Coronary Stent Implantation by Sealing the Arterial Puncture Site with a Vascular Hemostasis Device," *Catheterization and Cardiovascular Diag.*, vol. 30 (1993): 317–322.

William G. Kussmaul, III, M.D., et al., "Rapid Arterial Hemostasis and Decreased Access Site Complications After Cardiac Catheterization and Angioplasty: Results of a Randomized Trial of a Novel Hemostatic Device," *Journal of the American College of Cardiology*, vol. 25, No. 7 (1995) 1685–1692.

Pharmacia & Upjohn Manufacturer Brochure, "Gelfoam Sterile Powder," Feb. 1996.

Parmacia & Upjohn Manufacturer Brochure, "Gelfoam Sterile Powder," Mar. 1996.

Pharmacia & Upjohn Manufacturer Specification,"Gelfoam Sterile Sponge, Sterile Powder, and Sterile Film," Nov. 1996: 1–23.

S.A. Riley, et al., "Percutaneous Liver Biopsy with Plugging of Needle Tract: A Safe Method for Use in Patients with Impaired Coagulation," *The Lancer* (Aug. 1964).

Timothy A. Sanborn, M.D., et al., "Multicenter Randomized Trial Comparing a Percutaneous Collagen Hemostasis Device with Conventional Manual Compression After Diagnostic Angiography and Angioplasty," *Journal of the American College of Cardiology*, vol. 25, No. 7 (1995): 1685–1692.

R. Schrader, et al., "Collagen Application for Sealing of Arterial Puncture Sites in Comparison to Pressure Dressing A Randomized Trial," *Catheterizatiion, and Cardiovascular Diagnosis* (1992):298–302.

Sigmund Silber, M.D., "Rapid Hemostasis of Arterial Sites with Collagen in Patients Undergoing Diagnosis and Interventional Cardiac Catheterization," *Clinical Cardiology*, vol. 20 (Dec. 1997): 981–992.

Tony P. Smith, et al., "Percutaneous Transhepatic Liver Biopsy with Tract Embolization," *Radiology*, vol. 198 (1996): 769–774.

Marc Zins, M.D., et al., "US–guided Percutaneous Liver Biopsy with Plugging of the Needle Track: A Prospective Study in 72 High-Risk Patients," *Radiology*, vol. 184 (1992): 841–843.

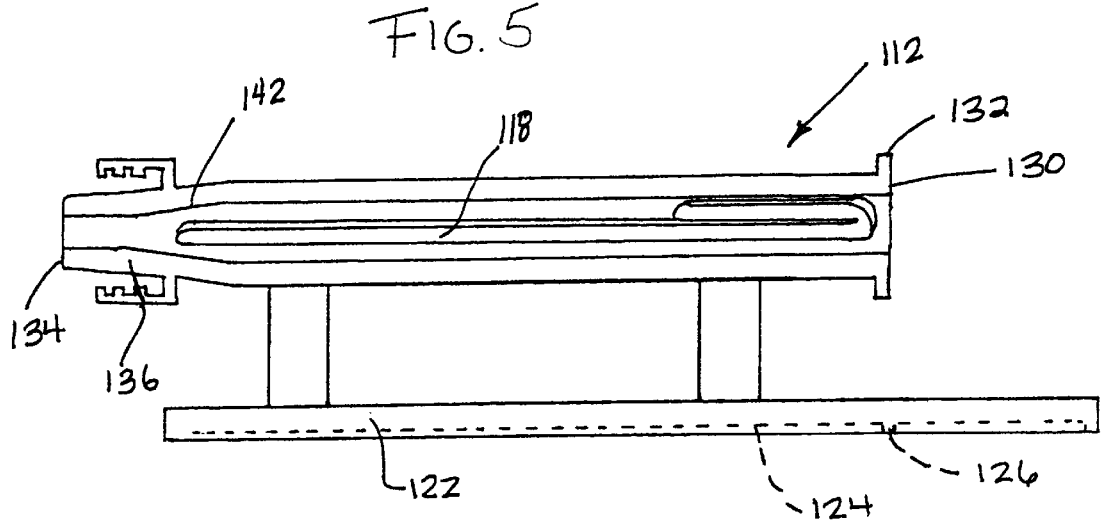
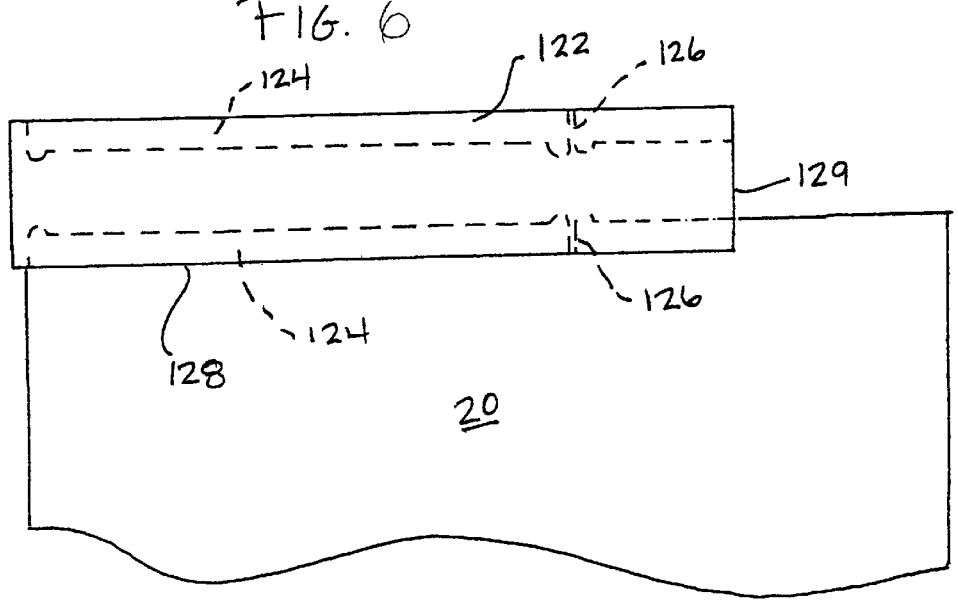

ABSORBABLE SPONGE WITH CONTRASTING AGENT

This application is a CIP of U.S. application Ser. No. 09/071,670, filed May 1, 1998 now U.S. Pat. No. 6,071,301 and U.S. application Ser. No. 09/071,284, filed May 1, 1998.

BACKGROUND OF THE INVENTION

1. Field of the Invention

The invention relates to an absorbable sponge, and more particularly, the invention relates to the delivery of a contrasting agent to a specific area or site in a mammal after a surgical or interventional procedure. The contrasting agent facilitates the location of the area or site even weeks or months after the initial procedure.

2. Brief Description of the Related Art

Percutaneous needle biopsy of solid organs is one of the most common interventional medical procedures. Millions of percutaneous needle biopsies are performed annually in the United States and throughout the world. Percutaneous biopsy is a safe procedure which has supplanted surgical biopsy for many indications, such as skin biopsy and liver biopsy.

Possible complications of needle biopsy include bleeding at the biopsy site. The amount of bleeding is related to a number of factors including needle size, tissue sample size, patient's coagulation status, and the location of the biopsy site. Vascular organs such as the liver, a common biopsy target, may bleed significantly after needle biopsy.

Sterile sponges, such as GELFOAM, are prepared in dry sterile sheets which are used as packing material during surgery for control of bleeding. The sponge sheets are left in the surgical site after surgery to stop bleeding and are absorbed by the body. A number of techniques have used these absorbable sterile sponge materials to plug a biopsy tract to minimize or prevent bleeding. The absorbable sponge provides a mechanical blockage of the tract, encourages clotting, and minimizes bleeding though the biopsy tract.

During the biopsy, a mechanic clip device is often attached to the site where tissue is removed, so that if further treatment is later required the location of the site can be identified. Unfortunately, the time period between the biopsy and treatment may be weeks during which time the clip may become dislodged thereby making it difficult to relocate the site.

Accordingly, it would be desirable to provide a reliable technique for identifying biopsy sites or puncture wound sites.

SUMMARY OF THE INVENTION

The present invention is based in part on the discovery that adding a contrasting agent (e.g, radiopaque agent) to an absorbable sponge provides for a material that not only facilitates hemostasis of a biopsy tract or other puncture wound but also permits precise identification of the site's location.

Accordingly, in one aspect, the invention is directed to a method for marking a bodily site in a patient that includes the steps of:

identifying the bodily site; and positioning a pledget of absorbable sponge material adjacent the bodily site wherein the absorbable sponge material includes a contrasting agent.

With the present invention, the exact location of the bodily site can be located many weeks or longer following positioning of the absorbable sponge material.

In another aspect, the invention is directed to a method for performing a biopsy that included the steps of:

removing tissue from a vascular tissue site; and positioning a pledget of absorbable sponge material adjacent the vascular tissue site wherein the absorbable sponge material includes a contrasting agent.

In another aspect, the invention is directed to a liquid permeable, absorbable, gelatin sponge that is prepared by a process that includes the steps of:

(a) preparing an aqueous gelatin solution;

(b) adding an organic solvent in the aqueous gelatin solution to form a second solution;

(c) incubating the second solution;

(d) forming a foam from the second solution wherein a contrasting agent is added to the second solution at any step prior to forming the foam; and (e) drying the foam.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 5 is a side cross sectional view of an alternative embodiment of an adaptor for delivery of a pledget including a template attached to the adaptor;

FIG. 6 is a top view of the template as it is used for cutting a pledget from an absorbable sponge sheet.

DETAILED DESCRIPTION OF THE PREFERRED EMBODIMENTS

Figure 1:
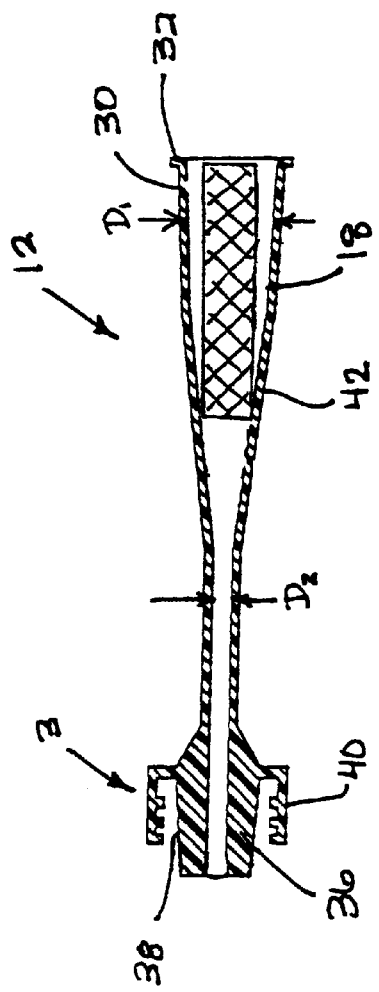
FIG. 1 is a side cross sectional view of an adaptor for delivery of a pledget to a needle.

The present invention is directed to an absorbable sponge material containing a contrasting agent. The absorbable sponge material is delivered to a specific area or site in a patient (i.e., mammal) after a surgical or interventional procedure. For example, the sponge material can be placed in the biopsy tract or other puncture wound and the contrasting agent enables marking or identification of the area or site. The absorbable sponge will be described in connection with treatment of a biopsy tract after a percutaneous needle biopsy. The absorbable sponge material can also exhibit secondary benefits of, for example, facilitating hemostasis and delivering therapeutic agents.

Prior to discussing the present invention in further detail, the following terms are defined:

"Pledget" means a piece of absorbable sponge containing a contrasting agent preferably of a generally elongated shape having a size which allows injection in a hydrated state through a biopsy needle or other cannula.

"Sponge" means a biocompatible material which is capable of being hydrated and is resiliently compressible in a hydrated state. Preferably, the sponge is non-inmmunogenic and is absorbable.

"Absorbable sponge" means a sponge which when implanted within a patient (i.e., human or other mammalian body) is absorbed by the body. The absorbable sponge contains a contrasting agent which may or may not be absorbable. Besides the contrasting agent, the sponge can also be used to deliver a beneficial agent such as thrombin, radiation treatment or the like.

"Bodily site" means any tissue in a mammal where the absorbable sponge containing the contrasting agent can be introduced. The invention is particularly suited for introducing the absorbable sponge into tissue sites where further treatment may be required, for example, as in the case following biopsy.

"Hydrate" means to partially or fully saturate with a fluid, such as, saline, water, or the like.

"Kneading" of the absorbable sponge material means both dry and wet manipulation of the sponge material which compresses, enlarges, or changes the shape of the sponge material causing the sponge material to have improved expansion response.

"Contrasting agent" means a biocompatible material that is capable of being detected or monitored by fluoroscopy, X-ray photography, CAT scan, ultrasound, or similar imaging techniques following placement into a mammalian subject. Preferred contrasting agents are radiopaque materials. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available. Other water insoluble contrast agents include gold, tungsten, and platinum powders. Some radiopaque contrasting agents are available in liquid form. These include, for example, OMNIPAQUE from Nycomed, Inc., Princeton, NJ. Preferably, the contrast agent is water insoluble (i.e., has a water solubility of less than 0.01 mg/ml at 20° C.).

The absorbable sponge material of the present invention is preferably a liquid permeable, water insoluble gelatin based sponge that has contrasting agent incorporated in the matrix of the sponge. By "incorporated" is meant that the contrasting agent is substantially dispersed throughout the sponge so that the contrasting material is not simply found on the periphery of the sponge. The sponge is made by mixing a suitable organic solvent (e.g., formaldehyde) with an aqueous solution of gelatin. The organic solvent facilitates the cross linkage of gelatin polymers. It is expected that glutaraldehyde may also be suitable. The resulting solution is then incubated typically at slightly above room temperature (30°–40° C.). Subsequently, a contrasting agent is added and the resulting mixture beaten to produce a firm foam. Thereafter, the foam is dried to produce the absorbable sponge material.

Typically, the aqueous gelatin solution containing 3–10% gelatin by weight is prepared as a warm solution (e.g., 80° C.) to help dissolve the gelatin. The solution is then allowed to cool (e.g, 35°–40° C.) before the organic solvent is added. A preferred organic solvent is formalin (an aqueous solution of formaldehyde). The amount of formalin used will control the hardness of the sponge and its rate of absorption into the body. The more formalin used, the harder the sponge and the lower the absorption rate. Typically, the amount used is between 0.01 to 10% based on the gelatin solution. The beating or whipping process takes about 5–15 or more minutes to produce a firm foam of about 4 to 8 times the volume of the original solution. The drying process initially begins with oven drying in the presence of circulating air at about 30° to 33°C. or higher and 10% humidity. After the foam is thoroughly dried, the foam can be heated to an elevated temperature of about 140° C. for a sufficient length of time (e.g., 3 hrs) until the sponge is firm. Suitable absorbable sponge materials are further described in U.S. Pat. No. 2,465,357 which is incorporated herein by reference.

It has been found that at least for contrasting agents that are not soluble in water, the contrasting agent must be added prior to beating the gelatin/formalin solution. The reason is that once the foam material is produced, the contrasting agent cannot be incorporated into the matrix of the sponge.

When employing contrasting agents that are liquids it is preferred that they be added to the gelatin/formalin solution prior to being beaten to form the foam product. This will insure that the contrasting agent is dispersed throughout the sponge.

Care should be taken when using insoluble contrasting agents not to overload the absorbable sponge material by using excessive amounts of contrasting agents. This will possibly result in sponges that have reduced cell structures, that is, the final volume will be significantly less than if no contrasting agent was used.

Following the above formulation, absorbable sponge materials containing different amounts of contrasting agent were prepared and tested. Specifically, 5 grams of pork gelatin (Bloom value 275) were mixed in 100 grams of water at 80° C. and the solution was allowed to cool to 35° C. before 0.03 cc of 40% formalin was added. The resulting solution was incubated at 35° C. for 2 hours before tantalum powder (50 to 150 grams) was added. The liquid was then vigorously mixed in a malt mixer to produce a foam. The foam was then oven dried at 35° C. for 12 hours.

The absorbable sponge material was examined with a fluoroscope and found to be extremely visible. Moreover, placement of the sponge material with contrasting agent in puncture sites of a swine model demonstrated that the absorbable sponge exhibited good hemostatic properties as well.

The sponge material with contrasting agent of the present invention is particularly suited for biopsies and other percutaneous procedures where knowledge of the site of initial treatment, e.g., tissue removal, is important.

While the absorbable sponge material can be employed with any suitable medical instrument, a preferred device and method for facilitating hemostasis of a biopsy tract is described herein to illustrate use of the absorbable sponge material. The technique is further described in U.S. patent application Ser. No. 09/247,880 entiled "Device and Method for Facilitating Hemostatis of a Biopsy Track" which application is incorprated herein by reference.

FIG. 1 shows the adaptor 12 in which the pledget 18 is placed for hydration and for delivery through the biopsy needle 16. The adaptor 12 allows pieces of absorbable sponge material with relatively large cross sections to be easily delivered through a biopsy needle 16 with a much smaller cross section. The adaptor 12 also functions to remove air from the pledget 18.

The adaptor 12 which delivers the hydrated pledget 18 to the needle 16 includes a first end 30 having an annular lip 32 or female luer fitting for connection to the syringe 14. A second end 34 of the adaptor 12 has a male luer fitting 36 for connection to a biopsy needle 16 or other cannula. The luer fitting 36 includes a tapered external surface 38 and a retaining ring 40 with internal threads for receiving an annular lip of the biopsy needle. The adaptor 12 has an internal lumen with a first diameter $D_1$ at the first end 30 and a second diameter $D_2$ at the second end 34. Between the first and second ends of the adaptor 12 a tapered section 42 of the adaptor provides a funnel for compressing the hydrated pledget 18 prior to injection through the biopsy needle 16 and needle hub 28.

The adaptor 12 may be formed in any known manner such as by molding from a plastic material. Preferably, the adaptor 12 is transparent so that the pledget 18 can be viewed through the adaptor and the user can visually monitor when the pledget is loaded within the adaptor and when the pledget has been delivered into the needle. The adaptor lumen may be provided with a friction reducing coating for improved delivery. The delivery fluid also reduces friction for improved delivery by wetting the exterior surface of the pledget 18.

Figure 2:
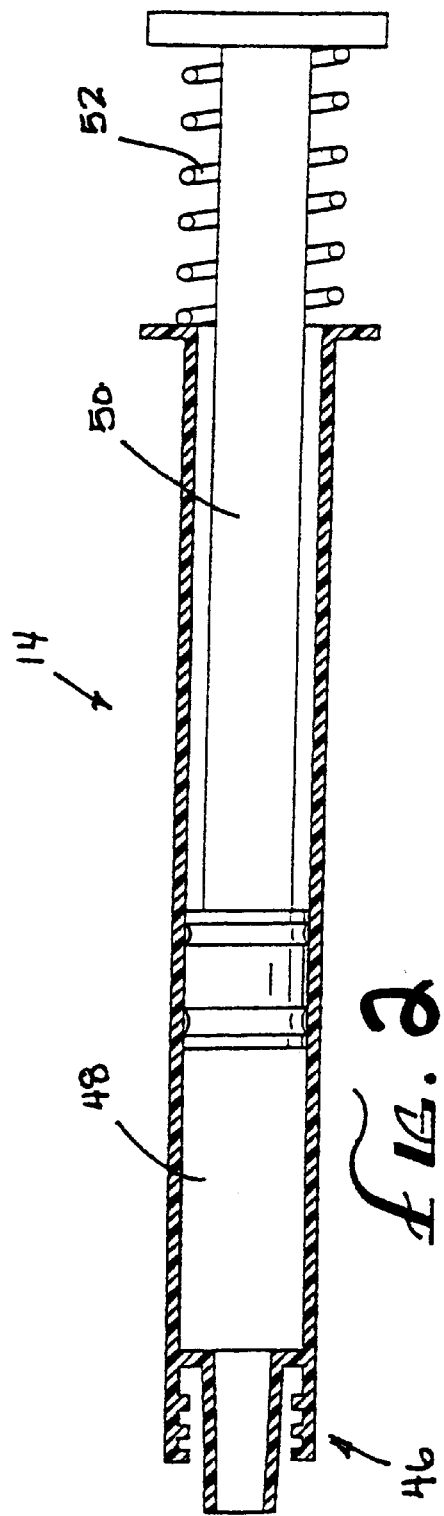
FIG. 2 is a side cross sectional view of a syringe for connection to the adaptor.

As shown in FIG. 2, the syringe 14 includes a male luer fitting 46, a fluid chamber 48, and a plunger 50. The first end 30 of the adaptor 12 is connectable to the luer fitting 46 of the conventional syringe 14. The syringe 14 may be provided with a spring 52 for automatic filling of the syringe 14 with a predetermined volume of fluid.

Figure 4:
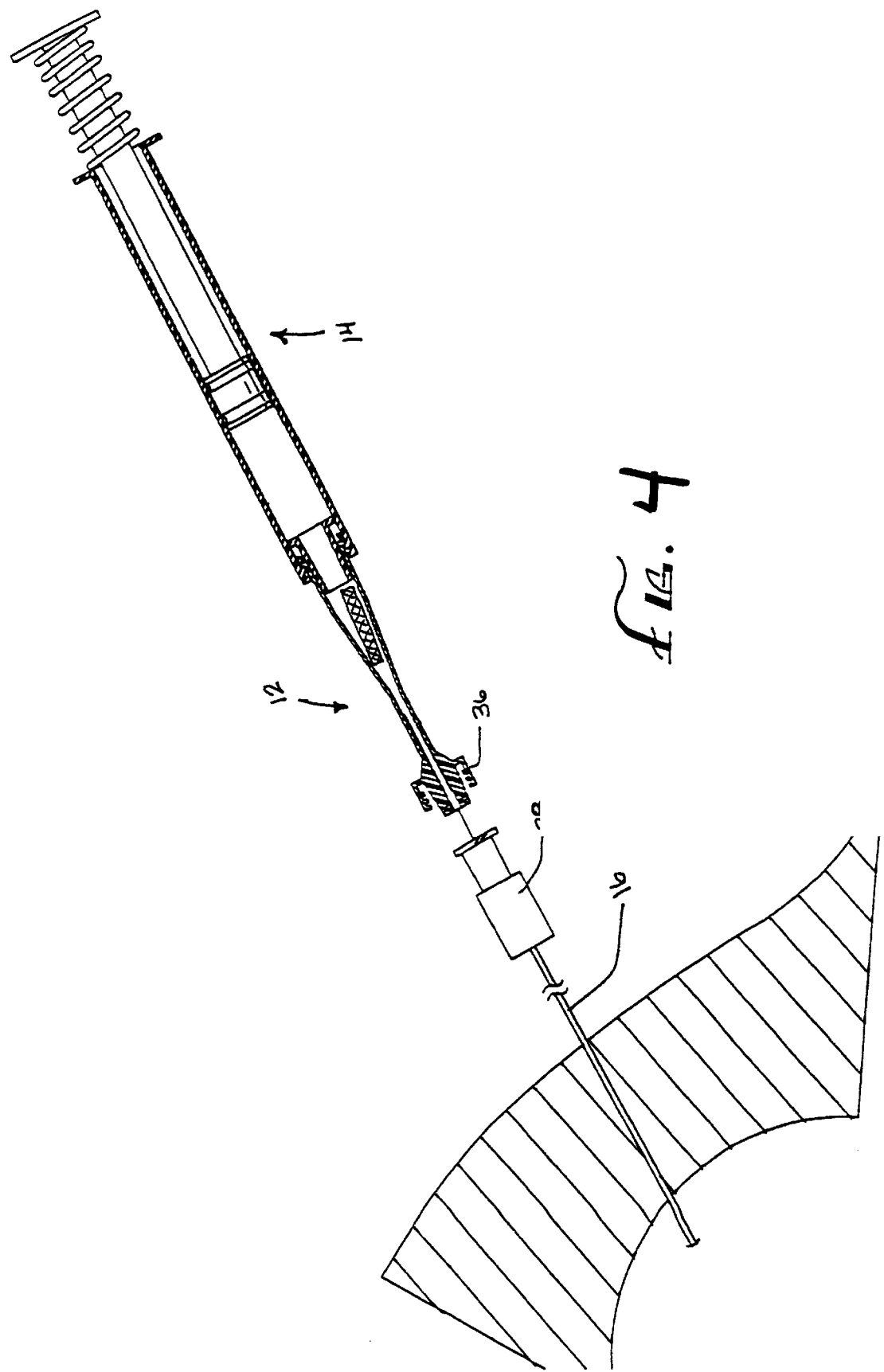
FIG. 4 is a side cross sectional view of the loaded adaptor and syringe combination in preparation for connection to a biopsy needle.

The biopsy needle 16 used with the present invention is preferably a co-axial biopsy needle, such as a bi-axial or a tri-axial biopsy needle. A co-axial biopsy needle includes an outer needle or cannula through which a tissue sample is removed with a tissue scoop or other biopsy instrument. Once the tissue sample has been removed, the outer cannula remains in the patient as illustrated in FIG. 4. Although the cannula for delivery of the sponge pledget has been described as a biopsy needle, the cannula may be a catheter, sheath, or any other type of cannula.

Figure 3:
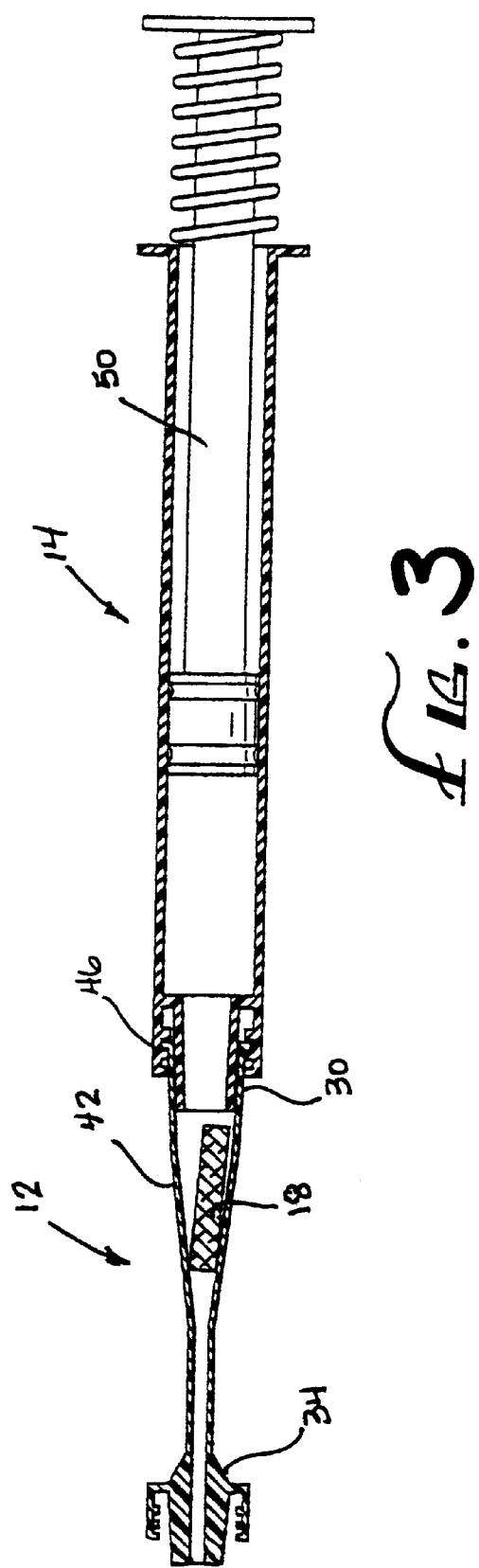
FIG. 3 is a side cross sectional view of an adaptor and syringe combination with a pledget positioned within the adaptor.

A preferred method of facilitating hemostasis of a biopsy tract will be described with reference to FIG. 3 which shows the loading and hydration of the pledget 18 within the adaptor 12. A pledget 18 is cut and placed within the adaptor 12 from the first end 30 of the adaptor. The syringe 14 is filled with a predetermined amount of fluid, such as saline, and is connected to the first end 30 of the adaptor 12 by the luer fitting 46. The plunger 50 of the syringe 14 is then depressed slowly causing fluid to pass into the adaptor 12, hydrating the pledget 18, and filling the adaptor with a column of fluid. Care should be taken to inject the fluid slowly to prevent the pledget from being ejected out of the second end 34 of the adaptor. Preferably, the user waits a few seconds once the fluid is injected into the adaptor 12 until the pledget 18 is adequately hydrated creating a lubricous surface on the pledget. The pledget 18 may expand within the adaptor to fill or nearly fill the lumen of the adaptor. The adaptor 12 with the pledget 18 hydrated within the proximal end is ready to inject the pledget into a biopsy tract to facilitate hemostasis within the biopsy tract. The adaptor 12 may be loaded prior to beginning the biopsy procedure.

After the biopsy procedure has been completed, the outer sheath of the biopsy needle 16 through which the biopsy has been taken is maintained in place within the biopsy tract, as shown in FIG. 4. The biopsy needle 16 provides preestablished targeting of the delivery site for delivery of the absorbable sponge pledget 18 and eliminates the uncertainty of re-access. The luer fitting 36 of the adaptor 12 is connected to the biopsy needle hub 28, as illustrated in FIG. 4. The biopsy needle 16 is withdrawn a short distance, such as about 1 to 20 mm, along the biopsy tract to provide space for the pledget 18 to be received in the biopsy tract. Additional fluid is then rapidly injected by the syringe to move the pledget 18 into the biopsy needle 16. When the adaptor lumen has been blocked by the hydrated pledget 18 which has swelled within the adaptor, injection of additional fluid will push the pledget through the tapered section 42 of the adaptor. If the adaptor lumen has not been entirely blocked by the pledget 18, the venturi effect will help draw the pledget through the tapered section 42 of the adaptor. After the pledget 18 is moved to the biopsy needle 16, the pledget 18 is then delivered from the needle 16 to the biopsy tract by rapid injection of additional fluid by the syringe 14. The hydrated pledget 18 quickly expands upon delivery to fill the available space in the biopsy tract to facilitate hemostasis and provide localized compression.

The absorbable sponge material of the present invention can be shaped into the required size by conventional means. Pledgets may be cut with a punch or a stencil or template and knife. Once hydrated, the pledget 18 can be easily compressed to fit into a lumen having a smaller cross sectional area than the original cross sectional area of the pledget. Additionally, the kneading of the hydrated pledget 18 during delivery encourages air trapped within the absorbable sponge to be expelled and replaced with fluid, allowing rapid expansion upon delivery.

When delivering a pledget 118 of absorbable sponge material, it is important to deliver a desired amount of the sponge material using a minimum amount of fluid.

Pledgets 118 with increased cross sectional area proximal ends may be prepared in a variety of manners. For example, if a pledget 118 is prepared from a sheet of sponge material, the increased proximal mass can be achieved by cutting the pledget with an enlarged proximal end. Alternatively, the pledget 118 may be formed by folding, rolling, compressing, or otherwise manipulating the sponge material to the desired shape. The proximal pledget mass may also be increased by adding separate pieces of material to the proximal end of the pledget. This additional material may be layered, wrapped, coiled or attached to the pledget in any other manner. The pledgets may also be formed by molding, bump extruding, dipping, or the like. The larger cross sectional area proximal end is generally about 1.2 to 4 times the cross sectional area of the distal end. In addition, the proximal end with the larger cross section area preferably extends along about ⅛ to ¾ of the total pledget length.

The pledget 118 illustrated in FIG. 5 has been formed by cutting a strip of material from an absorbable sponge sheet 20 with the aid of the template 122 as illustrated in FIG. 6. After the strip is cut, the proximal end of the strip is then folded back onto itself to form a pledget 118 with an increased cross sectional area and material mass at a proximal end. One example of a preferred embodiment of a pledget for delivery down a 20 gauge biopsy needle or cannula has a size of approximately 0.1×1.5×0.06 inches and is folded as illustrated in FIG. 5 to an overall length of about 0.9 inches. Placing this pledget 118 in an adaptor 112 having a largest internal diameter of 0.125 inches allows the pledget to be delivered to a 20 gauge or larger biopsy needle. Other common biopsy procedures use an 18 gauge or larger biopsy needle through a slightly larger guide cannula and would receive a somewhat larger pledget. After taking a core sample and removing the biopsy needle from the cannula guide, a pledget 118 may be delivered through the cannula to the biopsy site. The pledget 118 for use in the system employing an 18 gauge or larger biopsy needle may be formed from a strip which is approximately 0.11–0.12 inches wide by about 3.125 inches long with a thickness of about 0.06 inches and folded to an overall length of about 2.2 inches. This pledget having a 28 which is attached to the distal end of the adaptor.

As described above, the pledget may be delivered to the biopsy tract by holding the biopsy needle or cannula 16 stationary and injecting the pledget through the biopsy needle. If additional pledgets are to be delivered, the biopsy needle 16 is withdrawn a distance sufficient to accommodate an additional pledget and the additional pledget is then injected.

An alternative method of delivering the pledget into the biopsy tract includes withdrawing the biopsy needle or cannula 16 during delivery of the pledget 18 to deliver the pledget in an elongated trail which follows the biopsy tract. Placing the absorbable sponge material in a trail which fills the entire biopsy tract provides the added benefit of providing hemostasis along the entire biopsy tract. This is particularly helpful for stopping the bleeding of biopsy tracts in organs which tend to have excessive bleeding such as the liver, kidney, spleen, and other vascular organs.

In order to achieve a trail of absorbable sponge material in the biopsy tract, one method of the present invention involves the delivery of the pledget into the biopsy needle by a predetermined amount of fluid. The biopsy needle is then withdrawn at a velocity V while the pledget material is ejected from the biopsy needle at a velocity E with respect to the biopsy needle. The velocity V at which the biopsy needle is withdrawn is equal to or less than the velocity E at which the absorbable sponge material is delivered. The control of injection of fluid and withdrawal of the needle to achieve the desired trail of absorbable sponge material in the biopsy tract maybe controlled with an injection controlling device.

Figure 7:
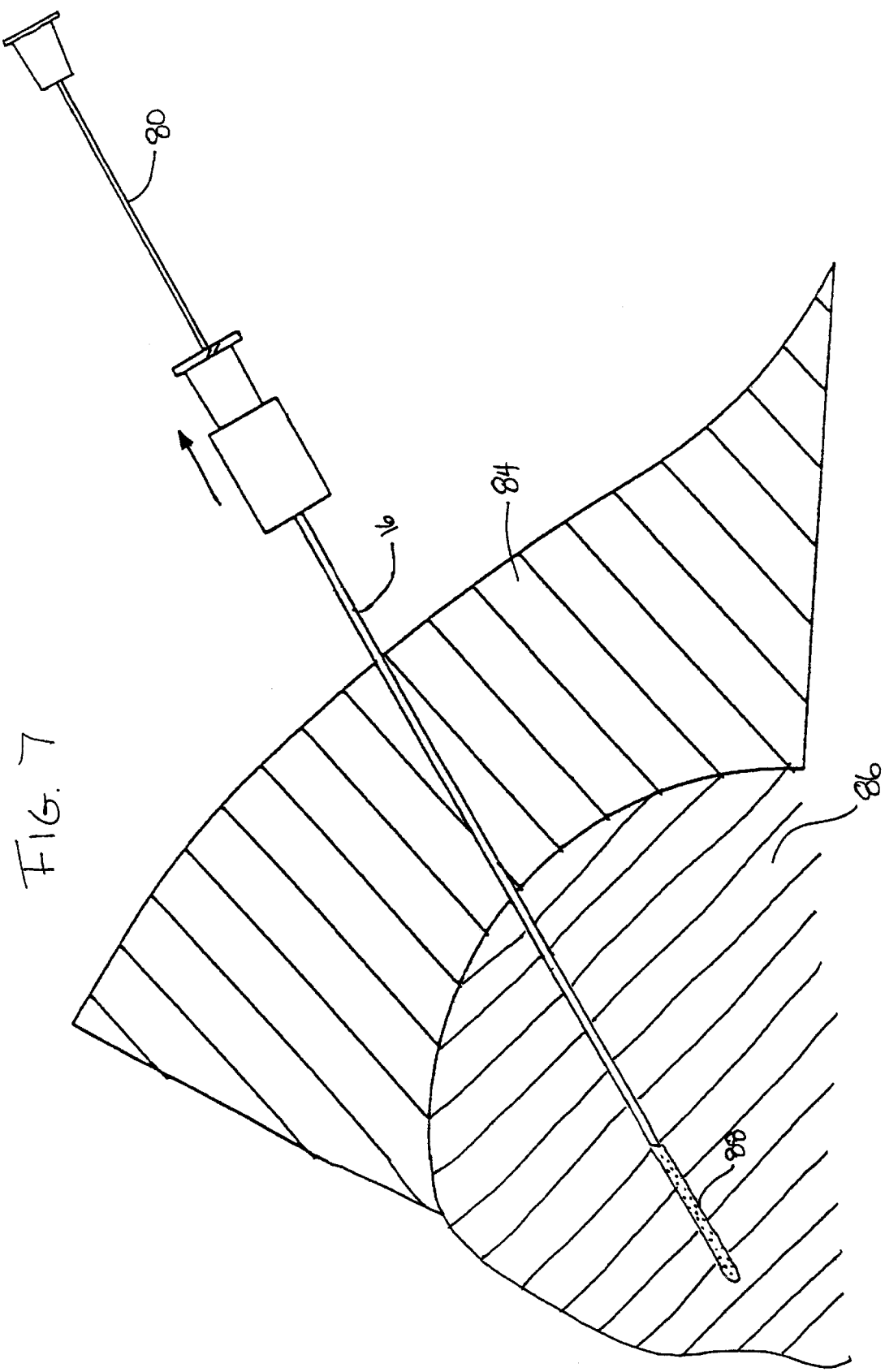
FIG. 7 is a side cross sectional view of a portion of an organ and a system for delivering a pledget into a biopsy tract in the organ.

According to an alternative embodiment as illustrated in FIG. 7, the adaptor may be used to deliver the pledget into the biopsy needle 16 and then the adaptor is removed from the biopsy needle. A plunger or stylet 80 which is generally provided with the biopsy needle 16 for inserting the biopsy needle is then used to deliver the pledget from the biopsy needle. As shown in FIG. 7, the biopsy needle extends through the tissue 84 and into the organ 86 for removal of a core of tissue. After biopsy, the pledget is injected into the needle 16 and the plunger 80 is placed within the biopsy needle so that a distal end of the plunger abuts the proximal end of the pledget 118. The plunger 80 is then held stationary while the biopsy needle 16 is withdrawn from the biopsy site. The plunger 80 causes the pledget 118 to be delivered in a trail 88 which fills the biopsy tract. The trail 88 preferably extends along the entire biopsy tract to or past a surface of the organ 86. The delivery of the trail 88 of absorbable sponge material provides an advantage over the delivery of discrete blobs of material because the trail is able to provide hemostasis along the entire tract. In contrast, if a blob of absorbable sponge material is delivered within the tract at a depth of 1–2 cm from the surface of the organs, this 1–2 cm of biopsy tract may continue to bleed significantly.

As an alternative to delivery of the pledget as a trail, the pledget may be delivered as a plug. To deliver a plug the plunger 80 is advanced into the needle 16 pushing the pledget out of the distal end of the needle while the needle is held stationary. A combination of delivery of plugs and trails may also be used. The pledget material may be delivered entirely within a single anatomical structure or may cross two or more anatomical structures such as an organ, surrounding tissue and facial layer.

In some instances it may be desirable to deliver multiple pledgets in spaced apart positions along the biopsy tract, particularly for a long biopsy tract. For delivery of additional pledgets, the biopsy needle 16 is retracted a distance sufficient to provide a space to accommodate an additional pledget 18 and the injection procedure described above is repeated for the additional pledget(s). For a particularly large biopsy site or cavity, additional pledgets 18 may be injected beside an initially injected pledget until the cavity is filled.

Although biopsy is most commonly performed by biopsy needle, biopsy may also be performed through other cannulas, such as catheters, long needles, endoscopes, or the like. The treatment procedure according to the present invention can be used for facilitating hemostasis of puncture wounds through different types of cannulas including needles, catheters, endoscopes, and the like. In addition, the treatment procedure and systems according to the present invention may be used to deliver absorbable or non-absorbable sponge for other therapys. For example, sponge may be delivered for cosmetic or reconstructive bulking or for temporary or permanent intravascular embolization.

In addition to the contrasting agent, the absorbable sponge pledget 18 may be used to deliver a beneficial agent, such as, thrombin, radiation treatment, or the like. The pledget can also be used to deliver therapeutic agents, such as radioactive isotopes for localized treatment of tumors, anti-cancer agents, antimetastatic agents, and the like. Examples of anti-cancer agents include 5-fluorouracil, cisplatin, prednisone, and others described in U.S. Pat. No. 4,619,913 which is incorporated herein by reference. The absorbable sponge pledget 18 may be presoaked with the beneficial agent for delivery to the biopsy tract. Alternatively, the pledget 18 may be hydrated with the beneficial liquid agent or the agent may be delivered to the pledget after the pledget is placed within the biopsy tract.

A pledget formed of inventive absorbable sponge material preferably will be absorbed by the body within 1 to 6 weeks. However, the pledget material may be designed to provide different rates of absorption. If the contrasting agent employed is also absorbable, the contrasting agent should be absorbed at approximately the same rate as the sponge material. Where the contrasting agent is non-absorbable, it will remain at the site.

While the invention has been described in detail with reference to the preferred embodiments thereof, it will be apparent to one skilled in the art that various changes and modifications can be made and equivalents employed, without departing from the present invention.

What is claimed is:

1. A method for marking a bodily site in a patient comprising the steps of:
   identifying the bodily site;
   positioning an absorbable sponge material substantially at the bodily site wherein the absorbable sponge material includes a contrasting agent that is substantially dispersed throughout the absorbable sponge material; and
   locating the position of the bodily site by detecting the contrasting agent.

2. The method of claim 1 wherein the contrasting agent is water insoluble.

3. The method of claim 2 wherein the contrasting agent is selected from the group consisting of tantalum, tantalum oxide, barium sulfate, gold, tungsten, and platinum and mixtures thereof.

4. The method of claim 1 wherein the contrasting agent is water soluble.

5. The method of claim 4 wherein the contrasting agent is selected from the group consisting of metrizamide, iopamidol, iothalamate sodium, iodomide sodium, and meglumine and mixtures thereof.

6. The method of claim 1 wherein the sponge material comprises a gelatin based sponge.

7. The method of claim 1 wherein the step of detecting the contrasting agent employs an imaging technique.

8. The method of claim 2 wherein the step of detecting the contrasting agent employs an imaging technique.

9. The method of claim 4 wherein the step of detecting the contrasting agent employs an imaging technique.

10. The method of claim 1 wherein the step of positioning the pledget comprises injecting the absorbable sponge through a cannula.

11. The method of claim 10 wherein the absorbable sponge is injected through a biopsy needle.

12. The method of claim 10 wherein the absorbable sponge is in a hydrated state.

13. The method of claim 1 wherein the pledget becomes absorbed within 1 to 6 weeks.

14. A method for contrasting a bodily site in a patient comprising the steps of:
   identifying the bodily site;
   positioning a biocompatible, liquid permeable absorbable sponge substantially at the bodily site wherein the sponge comprises a matrix that has a contrasting agent incorporated therein characterized in that the contrasting agent is substantially dispersed throughout the sponge; and
   locating the position of the bodily site by detecting the contrasting agent.

15. The method of claim 14 wherein the contrasting agent is water insoluble.

16. The method of claim 15 wherein the contrasting agent is selected from the group consisting of tantalum, tantalum oxide, barium sulfate, gold, tungsten, and platinum and mixtures thereof.

17. The method of claim 14 wherein the contrasting agent is water soluble.

18. The method of claim 17 wherein the contrasting agent is selected from the group consisting of metrizamide, iopamidol, iothalamate sodium, iodomide sodium, and meglumine and mixtures thereof.

19. The method of claim 14 wherein the sponge material comprises a gelatin based sponge.

20. The method of claim 14 wherein the step of detecting the contrasting agent employs an imaging technique.

21. The method of claim 15 wherein the step of detecting the contrasting agent employs an imaging technique.

22. The method of claim 17 wherein the step of detecting the contrasting agent employs an imaging technique.

23. The method of claim 14 wherein the step of positioning the absorbable sponge comprises injecting the absorbable sponge through a cannula.

24. The method of claim 23 wherein the absorbable sponge is injected through a biopsy needle.

25. The method of claim 23 wherein the absorbable sponge is in a hydrated state.

26. The method of claim 14 wherein the absorbable sponge becomes absorbed with in 1 to 6 weeks.

27. A method for contrasting a bodily site in a patient comprising the step of a
   positioning an absorbable sponge material substantially at the bodily site wherein the absorbable material includes a contrasting agent that is substantially dispersed throughout the absorbable sponge material.

28. The method of claim 27 further comprising the step of locating the position of the bodily site by detecting the contrasting agent.

29. The method of claim 27 wherein the absorbable sponge material is absorbed within 1 to 6 weeks.

30. The method of claim 27 further comprising the step of identifying the bodily site before positioning the absorbable sponge material.

* * * * *